(12) United States Patent
Ruman et al.

(10) Patent No.: US 10,327,963 B2
(45) Date of Patent: Jun. 25, 2019

(54) ABSORBENT ARTICLE HAVING A ZONED ATTACHMENT AREA FOR SECURING AN ABSORBENT ASSEMBLY TO A CHASSIS

(71) Applicant: Kimberly-Clark Worldwide, Inc., Neenah, WI (US)

(72) Inventors: Marcille Faye Ruman, Oshkosh, WI (US); Kathleen Irene Bennett, Neenah, WI (US); Michael D. Sperl, Waupaca, WI (US); Joseph J. Sina, Appleton, WI (US); Frédérique Vignali, Appleton, WI (US); Brandon Benjamin Kussow, De Pere, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 628 days.

(21) Appl. No.: 14/170,077

(22) Filed: Jan. 31, 2014

(65) Prior Publication Data
US 2015/0216735 A1    Aug. 6, 2015

(51) Int. Cl.
| | | |
|---|---|---|
| *A61F 13/15* | (2006.01) | |
| *A61F 13/20* | (2006.01) | |
| *A61F 13/496* | (2006.01) | |
| *A61F 13/49* | (2006.01) | |
| *A61F 13/56* | (2006.01) | |

(52) U.S. Cl.
CPC ........ *A61F 13/496* (2013.01); *A61F 13/4906* (2013.01); *A61F 13/565* (2013.01); *A61F 2013/49092* (2013.01); *A61F 2013/49095* (2013.01)

(58) Field of Classification Search
CPC ....................... A61F 13/4906; A61F 2013/583
See application file for complete search history.

(56) References Cited

U.S. PATENT DOCUMENTS

| | | | |
|---|---|---|---|
| 1,397,579 | A | 11/1921 | Guinzburg |
| 4,100,324 | A | 7/1978 | Anderson et al. |
| 4,205,679 | A | 6/1980 | Repke et al. |
| 4,573,986 | A | 3/1986 | Minetola et al. |
| 4,597,760 | A | 7/1986 | Buell |
| 4,610,681 | A | 9/1986 | Strohbeen et al. |
| 4,663,220 | A | 5/1987 | Wisneski et al. |

(Continued)

FOREIGN PATENT DOCUMENTS

| | | |
|---|---|---|
| EP | 0459178 | 12/1991 |
| EP | 0217032 | 2/1992 |

(Continued)

OTHER PUBLICATIONS

International Search Report and Written Opinion of International Application No. PCT/IB2015/050621, dated May 1, 2015, 11 pages.

*Primary Examiner* — Michele M Kidwell
(74) *Attorney, Agent, or Firm* — Armstrong Teasdale LLP (57) ABSTRACT

An absorbent article includes a chassis and an absorbent assembly. The absorbent assembly is formed separately from the chassis, and attached to the chassis by an attachment area. The attachment area includes a front attachment zone, a rear attachment zone, and a central attachment zone extending between the front and rear attachment zones. The front and rear attachment zones have a first width and a second width, respectively, and the central attachment zone has a third width less than the first and second widths.

20 Claims, 6 Drawing Sheets

(56) References Cited

U.S. PATENT DOCUMENTS

| | | |
|---|---|---|
| 4,664,663 A | 5/1987 | Brier |
| 4,699,621 A | 10/1987 | Stevens et al. |
| 4,701,172 A | 10/1987 | Stevens |
| 4,747,846 A | 5/1988 | Boland et al. |
| 4,846,825 A | 7/1989 | Enloe et al. |
| 4,940,464 A | 7/1990 | Van Gompel et al. |
| 5,000,806 A | 3/1991 | Merkatoris |
| 5,046,272 A | 9/1991 | Vogt et al. |
| 5,064,421 A | 11/1991 | Tracy |
| 5,104,116 A | 4/1992 | Pohjola |
| 5,224,405 A | 7/1993 | Pohjola |
| 5,226,992 A | 7/1993 | Morman |
| 5,236,430 A | 8/1993 | Bridges |
| 5,284,703 A | 2/1994 | Everhart et al. |
| 5,350,624 A | 9/1994 | Georger et al. |
| 5,385,775 A | 1/1995 | Wright |
| 5,476,458 A | 12/1995 | Glaug et al. |
| 5,482,765 A | 1/1996 | Bradley et al. |
| 5,486,166 A | 1/1996 | Bishop et al. |
| 5,490,846 A | 2/1996 | Ellis et al. |
| 5,492,751 A | 2/1996 | Butt, Sr. et al. |
| 5,496,429 A | 3/1996 | Hasse et al. |
| 5,500,063 A | 3/1996 | Jessup |
| 5,593,401 A | 1/1997 | Sosalla et al. |
| 5,601,544 A | 2/1997 | Glaug et al. |
| 5,607,416 A | 3/1997 | Yamamoto et al. |
| 5,624,420 A | 4/1997 | Bridges et al. |
| 5,624,424 A | 4/1997 | Sausaka et al. |
| 5,662,638 A | 9/1997 | Johnson et al. |
| 5,706,524 A | 1/1998 | Herrin et al. |
| 5,714,156 A | 2/1998 | Schmidt et al. |
| 5,766,389 A | 6/1998 | Brandon et al. |
| 5,772,825 A | 6/1998 | Schmitz |
| 5,779,831 A | 7/1998 | Schmitz |
| 5,820,973 A | 10/1998 | Dodge, II et al. |
| 5,870,778 A | 2/1999 | Tharpe et al. |
| 5,885,266 A | 3/1999 | Chihani et al. |
| 6,057,024 A | 5/2000 | Mleziva et al. |
| 6,113,717 A | 9/2000 | Vogt et al. |
| 6,369,291 B1 | 4/2002 | Uchimoto et al. |
| 6,380,292 B1 | 4/2002 | Gibes et al. |
| 6,383,170 B1 | 5/2002 | Mishima et al. |
| 6,394,991 B1 | 5/2002 | Takei et al. |
| 6,552,245 B1 | 4/2003 | Roessler |
| 6,562,017 B1 | 5/2003 | Nakaoka et al. |
| 6,576,809 B1 | 6/2003 | Inoue et al. |
| 6,585,840 B2 | 7/2003 | Rabe et al. |
| 6,605,071 B1 | 8/2003 | Gray et al. |
| 6,605,173 B2 | 8/2003 | Glaug et al. |
| 6,645,190 B1 | 11/2003 | Olson et al. |
| 6,753,455 B2 | 6/2004 | Chmielewski |
| 6,822,136 B1 | 11/2004 | Niemeyer et al. |
| 6,899,780 B2 | 5/2005 | Rajala et al. |
| 6,916,750 B2 | 7/2005 | Thomas et al. |
| 6,939,335 B2 | 9/2005 | Franke et al. |
| 6,962,578 B1 | 11/2005 | Lavon et al. |
| 6,969,378 B1 | 11/2005 | Vukos et al. |
| 6,969,441 B2 | 11/2005 | Welch et al. |
| 7,014,632 B2 | 3/2006 | Takino et al. |
| 7,047,572 B2 | 5/2006 | Hopkins |
| 7,227,051 B2 | 6/2007 | Mitsui et al. |
| 7,264,686 B2 | 9/2007 | Thorson et al. |
| 7,666,175 B2 | 2/2010 | Trennepohl |
| 7,727,217 B2 | 6/2010 | Hancock-Cooke |
| 7,777,094 B2 | 8/2010 | Mori et al. |
| 7,794,441 B2 | 9/2010 | Ashton et al. |
| 7,803,244 B2 | 9/2010 | Siqueira et al. |
| 7,854,022 B2 | 12/2010 | Warren et al. |
| 7,901,390 B1 | 3/2011 | Ashton et al. |
| 8,109,916 B2 | 2/2012 | Wennerback |
| 8,168,028 B2 | 5/2012 | Schneider et al. |
| 8,212,102 B2 | 7/2012 | Kumasaka |
| 8,282,616 B2 | 10/2012 | Lehto et al. |
| 8,361,913 B2 | 1/2013 | Siqueira |
| 2002/0092604 A1 | 7/2002 | McCabe et al. |
| 2002/0143316 A1 | 10/2002 | Sherrod et al. |
| 2002/0177829 A1 | 11/2002 | Fell |
| 2003/0000620 A1 | 1/2003 | Herrin et al. |
| 2003/0163104 A1 | 8/2003 | Tears et al. |
| 2004/0064125 A1 | 4/2004 | Justmann et al. |
| 2004/0102757 A1 | 5/2004 | Olson |
| 2006/0149208 A1 | 7/2006 | Carr |
| 2006/0247591 A1 | 11/2006 | Hughes et al. |
| 2007/0073262 A1 | 3/2007 | Babusik et al. |
| 2007/0173782 A1* | 7/2007 | LaVon ............. A61F 13/49413 604/396 |
| 2007/0208318 A1 | 9/2007 | Loritz et al. |
| 2008/0132863 A1* | 6/2008 | Waksmundzki .. A61F 13/49014 604/367 |
| 2008/0134487 A1 | 6/2008 | Harlono |
| 2008/0287897 A1 | 11/2008 | Guzman Reyes et al. |
| 2009/0157034 A1 | 6/2009 | Mattingly et al. |
| 2010/0049155 A1 | 2/2010 | Soderbergh et al. |
| 2010/0063468 A1 | 3/2010 | Lehto et al. |
| 2010/0076390 A1 | 3/2010 | Norrby et al. |
| 2010/0179503 A1 | 7/2010 | Roe et al. |
| 2011/0092941 A1 | 4/2011 | Ruman et al. |
| 2011/0125122 A1 | 5/2011 | Thorson et al. |
| 2011/0144611 A1 | 6/2011 | Saito |
| 2012/0241078 A1 | 9/2012 | Schlinz |
| 2012/0244078 A1 | 9/2012 | Schlinz et al. |
| 2012/0316523 A1 | 12/2012 | Hippe et al. |
| 2013/0304013 A1* | 11/2013 | Goerg-Wood ...... A61F 13/5611 604/387 |
| 2013/0338623 A1* | 12/2013 | Kinoshita ......... A61F 13/49011 604/385.29 |
| 2014/0257226 A1* | 9/2014 | Wang ................... A61F 13/539 604/385.14 |

FOREIGN PATENT DOCUMENTS

| | | |
|---|---|---|
| EP | 0638304 | 3/1999 |
| EP | 0941727 | 9/1999 |
| EP | 0955976 | 3/2002 |
| EP | 2022453 | 2/2009 |
| GB | 2250921 | 6/1992 |
| JP | 2007195792 | 8/2007 |
| KR | 20030090656 A | 11/2003 |
| WO | 0037009 | 6/2000 |
| WO | 0188245 | 11/2001 |
| WO | 02069871 A1 | 9/2002 |

* cited by examiner

ABSORBENT ARTICLE HAVING A ZONED ATTACHMENT AREA FOR SECURING AN ABSORBENT ASSEMBLY TO A CHASSIS

FIELD

The present invention relates generally to absorbent articles intended for personal wear and, more particularly, to an absorbent article having a chassis and an absorbent assembly wherein the absorbent assembly is attached to the chassis by a zoned attachment area.

BACKGROUND

Exemplary absorbent articles include training pants, diapers, incontinence products, disposable underwear, medical garments, absorbent swim wear, and the like. Training pants (albeit, not exclusively) are disposable absorbent articles configured for use in the toilet training process. Toilet training is a process that includes many training techniques and aids that can be used by parents or other caregivers. One aspect of the total toilet training process is changing from the use of diapers to the use of training pant to help the child understand that he or she should now use the toilet.

Many caregivers underestimate the difficulty of teaching the toilet training process to young children. If a child does not respond to an initial toilet training instruction or introduction, the caregiver can be at a loss for finding techniques, methods, or teaching tools to encourage the child to master the art of toilet training. Thus, while various teaching tools such as books, videotapes, charts with stickers, personalized toilets, and interactive toilet training kits are available, there remains a need for improved motivational mechanisms to facilitate the toilet training process.

One motivational mechanism is the use of training pants having an improved aesthetic appearance. Specifically, a child is encouraged to wear a garment that resembles underwear worn by older children. Thus, there is an ongoing need to increase the appeal of the toilet training process to children, and to improve the aesthetic appearance of training pant. However, it is important that any modifications to the training pant to meet these needs do not compromise the use of the articles or any functional features of the articles (e.g., wetness indicators).

Accordingly, there is a need for a training pant having an aesthetic appearance similar to conventional underwear, which also has the same or improved performance as compared to known training pants.

SUMMARY

In one aspect, an absorbent article generally comprises a chassis and an absorbent assembly. The absorbent assembly is formed separately from the chassis, and attached to the chassis by an attachment area. The attachment area includes a front attachment zone, a rear attachment zone, and a central attachment zone extending between the front and rear attachment zones. The front and rear attachment zones have a first width and a second width, respectively, and the central attachment zone has a third width less than the first and second widths.

In another aspect, an absorbent article generally comprises a chassis having a pair of laterally opposing side edges defining leg openings of the article when the article is in a wear configuration, a leg elastic member disposed along each side edge of the chassis, and an absorbent assembly attached to the chassis by an attachment area. The attachment area includes a longitudinally extending zone of reduced width disposed between the leg elastic members.

In yet another aspect, an absorbent article includes a front waist region, a back waist region, and a crotch region. The absorbent article generally comprises a chassis having a pair of laterally opposing side edges within the crotch region of the absorbent article, a leg elastic member disposed along each side edge of the chassis, and an absorbent assembly attached to the chassis by an attachment area. The absorbent assembly has laterally opposing non-attachment zones along the crotch region of the absorbent article configured to facilitate elastic retraction and extension of the leg elastic members.

Other features of this disclosure will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
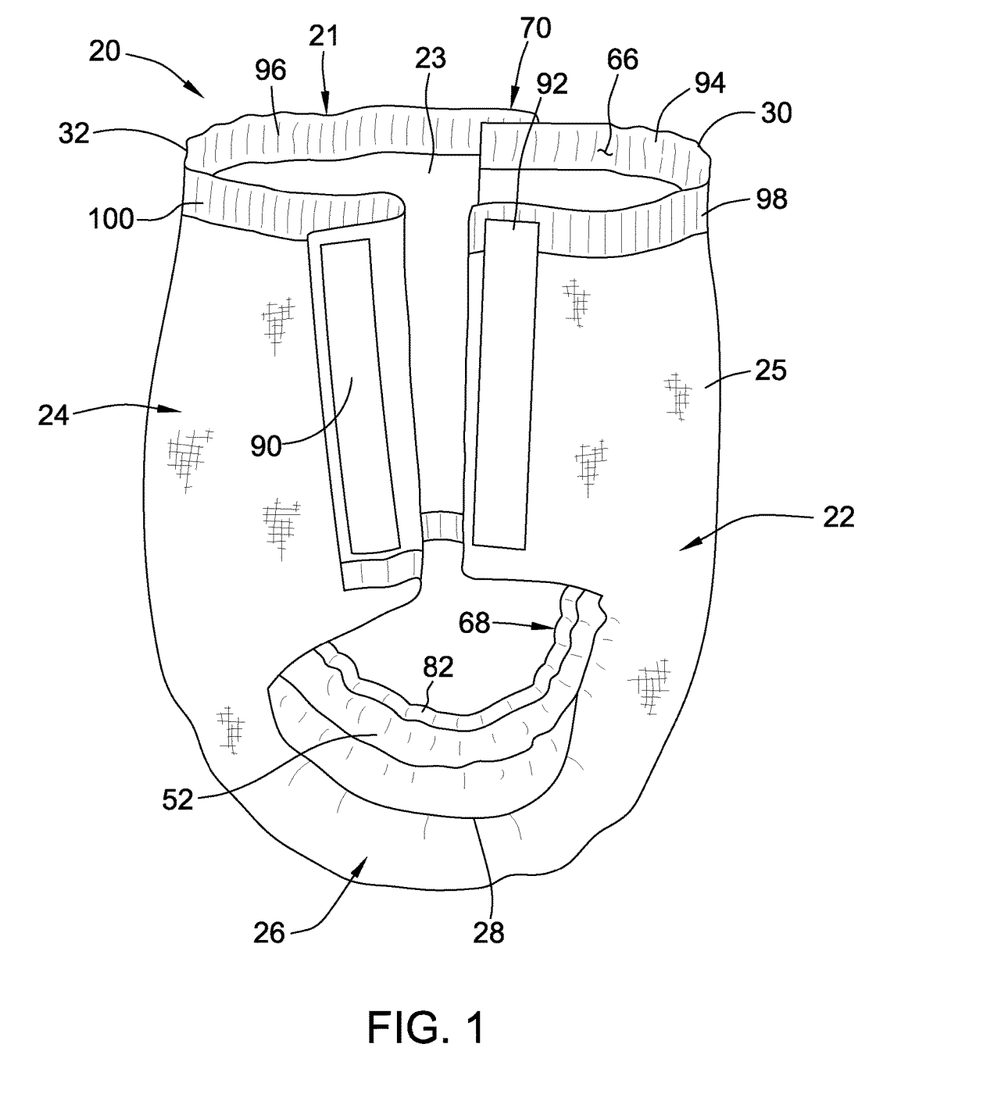
FIG. 1 is a side perspective of one suitable embodiment of an absorbent article shown in the form of a training pant, the training pant having a chassis and an absorbent assembly secured to the chassis.

Referring now to the drawings and in particular to FIG. 1, one suitable embodiment of an absorbent article is illustrated in the form of a child's toilet training pant and is indicated in its entirety by the reference numeral 20. The term absorbent article generally refers to articles that may be placed against or in proximity to a body of a wearer to absorb and/or retain various exudates from the body. The absorbent training pant 20 may or may not be disposable. Disposable refers to articles that are intended to be discarded after a limited period of use instead of being laundered or otherwise conditioned for reuse. It is understood that the embodiments of the present disclosure are suitable for use with various other absorbent articles intended for personal wear, including but not limited to diapers, swim diapers, feminine hygiene products (e.g., sanitary napkins), incontinence products, medical garments, surgical pads and bandages, other personal care or health care garments, and the like without departing from the scope of the present disclosure.

By way of illustration only, various materials and methods for constructing training pant such as the pant 20 of the present disclosure are disclosed in U.S. patent application Ser. No. 14/062,278 filed Oct. 24, 2013 by Ruman et al.; U.S. patent application Ser. No. 14/068,918 filed Oct. 31, 2013 by Sina et al.; U.S. patent application Ser. No. 14/068,913 filed Oct. 31, 2013 by Bennett et al.; PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al., which are incorporated herein by reference.

Figure 2:
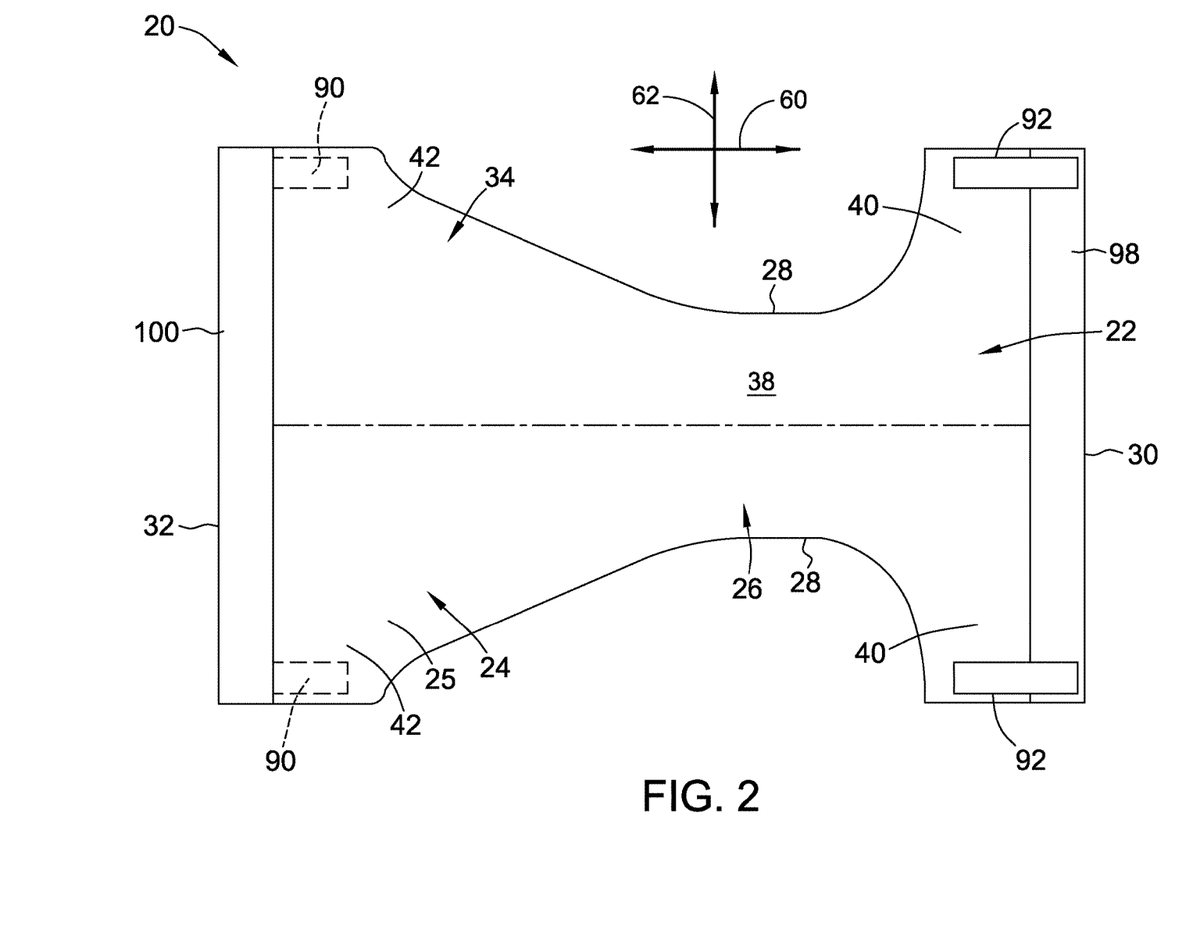
FIG. 2 illustrates a bottom plan view of the absorbent article of FIG. 1 with the training pant in an unfastened, unfolded and laid flat condition, and showing a surface of the training pant adapted to face away from the wearer during use.
Figure 3:
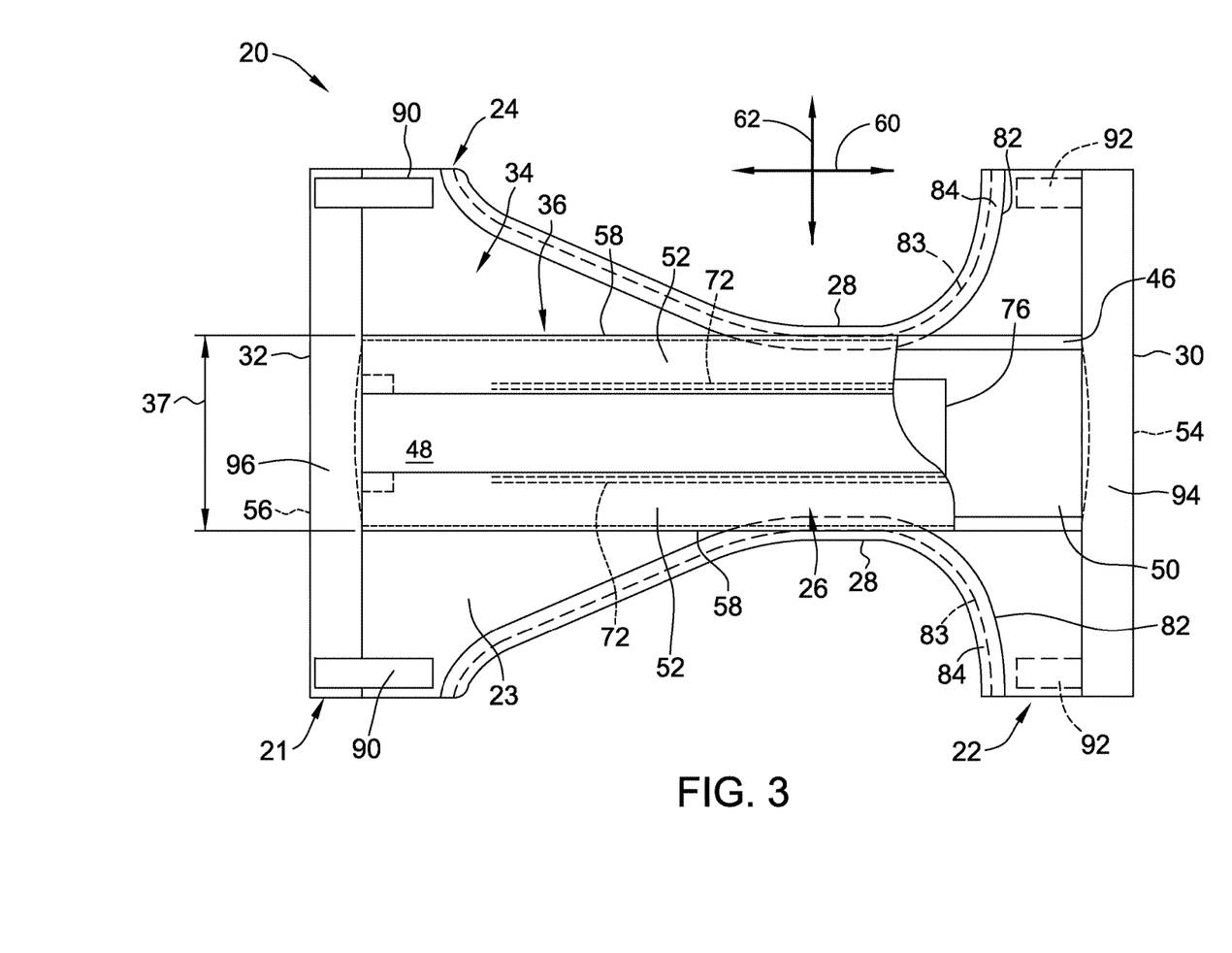
FIG. 3 illustrates a top plan view similar to FIG. 2 but showing a surface of the training pant adapted to face the wearer during use, portions of the training pant being cut away to show underlying features.

As seen in FIGS. 1-3, the training pant 20 has a front waist region 22, a back waist region 24, and a crotch region 26 disposed longitudinally between and interconnecting the front and back waist regions. The front waist region 22, the back waist region 24 and the crotch region 26 are indicated generally by the respective reference numbers. The training pant 20 also has a pair of laterally opposite side edges 28 and a pair of longitudinally opposite waist edges, respectively designated front waist edge 30 and back waist edge 32. In the illustrated embodiment, the side edges 28 are arcuately shaped to provide the training pant 20 with a more body conforming shape. The front waist region 22 is contiguous with the front waist edge 30, and the back waist region 24 is contiguous with the back waist edge 32.

With reference to FIGS. 2 and 3, the training pant 20 includes a chassis, indicated generally at 34, and an absorbent assembly, indicated generally at 36, attached to the chassis 34. Arrows 60 and 62 in FIGS. 2 and 3 depict the orientation of a longitudinal axis and a transverse or lateral axis, respectively, of the training pant 20. The training pant 20 also includes a body-facing side 23 (i.e., the side of the training pant 20 that faces the body of a wearer when worn) and a garment-facing side 25 (i.e., the side of the training pant 20 that faces away from the body of a wearer when worn).

The illustrated absorbent assembly 36 extends longitudinally from the front waist region 22 through the crotch region 26 to the back waist region 24. While the illustrated absorbent assembly 36 is shown and described herein as extending from the crotch region 26 into both the front and back waist regions 22 and 24, it is contemplated that the absorbent assembly 36 may extend from the crotch region 26 into primarily the front waist region 22, or into primarily the back waist region 24, without departing from some aspects of this disclosure. Further, the absorbent assembly 36 may extend any suitable length along the crotch region 26 and/or into the front waist region 22 and/or the back waist region 24. In the illustrated embodiment, the chassis 34 and the absorbent assembly 36 are formed separately from one another. It is contemplated, however, that the chassis 34 and the absorbent assembly 36 may be integrally formed with one another in some embodiments. It is further contemplated that in some suitable embodiments the absorbent assembly 36 can be disposable and the chassis 34 can be non-disposable.

As seen in FIG. 2, the chassis 34 includes a longitudinally extending central portion 38, a pair of laterally opposite front side portions 40 extending outward from the central portion 38 at the front waist region 22 (thereby forming transversely outer portions of the front waist region, and more broadly in part forming transversely opposite sides of the training pant), and a pair of laterally opposite back side portions 42 extending outward from the central portion at the back waist region 24 (thereby forming transversely outer portions of the back waist region, and together with the front side portions 40 further defining the sides of the pant). In the illustrated embodiment, the central portion 38 extends from the front waist region 22 through the crotch region 26 to the back waist region 24 of the training pant 20.

In one suitable embodiment and as seen in FIG. 2, the front side portions 40, the back side portions 42, and the central portion 38 are formed from the same sheet of material. In other suitable embodiments, one or more of the front side portions 40, the back side portions 42, and/or the central portion 38 may be formed from two or more separate elements. For example, in one suitable embodiment (see, e.g., FIG. 6), the front side portions 40 and/or the back side portions 42 can be formed separately from and attached to the central portion 38.

The chassis 34 may comprise any suitable material including, for example and without limitation, a liquid permeable material that provides a generally cloth-like texture. The chassis 34 can be a single layer of material, or a multi-layered laminate structure. The chassis 34 or portions thereof may also be made of those materials of which the liquid permeable bodyside liner 48 is made. In other suitable embodiments, it is contemplated that the chassis 34 can be liquid impermeable. It is further contemplated that the chassis 34 can be vapor impermeable or vapor permeable (i.e., "breathable"). One suitable "breathable" material is composed of a microporous polymer film or a nonwoven fabric that has been coated or otherwise treated to impart a desired level of liquid impermeability.

It is also contemplated that the chassis 34 may be stretchable, and more suitably elastic. In particular, the chassis 34 is suitably stretchable and more suitably elastic in at least the transverse, or circumferential direction of the pant 20. In other embodiments, the chassis 34 may be stretchable, and more suitably elastic, in both the transverse and the longitudinal direction. It is contemplated that the chassis 34 can be stretchable in any suitable direction.

The absorbent assembly 36 of the illustrated embodiment is attached to the chassis 34 along at least the crotch region 26 of the absorbent training pant 20, as described in more detail below. While the absorbent assembly 36 illustrated in FIG. 3 is shown and described herein as being attached to the chassis 34 along the crotch region 26, it is contemplated that the absorbent assembly 36 may be attached to the chassis 34 along any one or more of the crotch region 26, the front waist region 22, and/or the back waist region 24, without departing from the scope of this disclosure. Further, the absorbent assembly 36 may be attached to the chassis 34 along any suitable length and/or area of the chassis 34.

As seen in FIG. 3, the illustrated absorbent assembly 36 is generally rectangular in shape having a front end 54, a back end 56, and longitudinally extending side edges 58 defining a width 37 of the absorbent assembly 36. It is contemplated that the absorbent assembly 36 may have other suitable shapes without departing from the scope of the present disclosure including, for example, an hour-glass shape, a "T"-shape, and an "I"-shape. In the illustrated embodiment, the front and back ends 54, 56 of the absorbent assembly 36 extend to the front and back waist edges 30, 32 of the training pant 20, respectively, and define respective portions of the front and back waist edges 30, 32. It is contemplated, however, that the front end 54 and/or the back end 56 of the absorbent assembly 36 can be spaced inward from the front and back waist edges 30, 32 of the training pant 20. In such an embodiment, the front and back waist edges 30, 32 of the training pant 20 are defined solely by the chassis 34. As illustrated in FIG. 3, the side edges 58 of the absorbent assembly 36 can be spaced slightly inward from the side edges 28 of the absorbent training pant 20, which in the illustrated embodiment are defined by the chassis 34. In other suitable embodiments, the opposite side edges 58 of the absorbent assembly 36 can form portions of the side edges 28 of the absorbent training pant 20.

In one suitable embodiment and as illustrated in FIG. 3, the absorbent assembly 36 comprises a liquid impermeable backsheet 46 and a bodyside liner 48 attached to the backsheet in a superposed relation by suitable means such as adhesives, ultrasonic bonds, pressure bonds, thermal bonds or other conventional techniques. An absorbent structure (or absorbent core) 50 is disposed between the backsheet 46 and the bodyside liner 48. A pair of containment flaps 52 is integrally formed from the absorbent assembly 36 for inhibiting the lateral flow of body exudates.

In one suitable embodiment, the backsheet comprises a material which is substantially liquid impermeable. The backsheet 46 can be a single layer of liquid impermeable material, or may comprise a multi-layered laminate structure in which at least one of the layers is liquid impermeable. Multiple layers of the backsheet 46 may be suitably joined together by an adhesive, ultrasonic bonds, pressure bonds, thermal bonds, or the like. Suitable adhesives can be applied continuously or intermittently as beads, a spray, parallel swirls, or the like.

The backsheet 46 can be both liquid and vapor impermeable, or, more suitably, it may be liquid impermeable and vapor permeable. The backsheet 46 can be manufactured from a thin plastic film, although other flexible liquid impermeable materials may also be used. The backsheet 46 prevents waste material from wetting articles, such as bed sheets and clothing, as well as the wearer and caregiver. In one suitable embodiment, the liquid impermeable material can permit vapors to escape from the interior of the disposable absorbent article, while still preventing liquids from passing through the backsheet 46. One suitable "breathable" material is composed of a microporous polymer film or a nonwoven fabric that has been coated or otherwise treated to impart a desired level of liquid impermeability.

It is also contemplated that the backsheet 46 may comprise a liquid permeable material, or the backsheet 46 may be omitted from the absorbent assembly 36 altogether. In such embodiments, the chassis 34 suitably comprises a liquid impermeable material to provide a liquid barrier to body exudates. In one embodiment in which the backsheet 46 is omitted, the bodyside liner 48 is attached to the chassis 34 such that the absorbent structure 50 is disposed between the bodyside liner 48 and the inner surface of the chassis 34. In another suitable embodiment, both the absorbent structure 50 and the bodyside liner 48 are attached to the chassis 34.

It is also contemplated that the backsheet 46 may be stretchable, and more suitably elastic. In particular, the backsheet 46 is suitably stretchable and more suitably elastic in at least the transverse, or circumferential direction of the pant 20. In other embodiments the backsheet 46 may be stretchable, and more suitably elastic, in both the transverse and the longitudinal direction.

The bodyside liner 48 is suitably compliant, soft-feeling, and non-irritating to the wearer's skin. The bodyside liner 48 is also sufficiently liquid permeable to permit liquid body exudates to readily penetrate through its thickness to the absorbent structure 50. Further, the bodyside liner 48 can be less hydrophilic than the absorbent structure 50 to present a relatively dry surface to the wearer and permit liquid to readily penetrate through its thickness. The hydrophilic/hydrophobic properties can be varied across the length, width and/or depth of the bodyside liner 48 and absorbent structure 50 to achieve the desired rate of fluid intake and dryness.

A suitable bodyside liner 48 may be manufactured from a wide selection of web materials, such as porous foams, reticulated foams, apertured plastic films, woven and nonwoven webs, or a combination of any such materials. For example, the bodyside liner 48 may comprise a meltblown web, a spunbonded web, or a bonded-carded-web composed of natural fibers, synthetic fibers or combinations thereof. The bodyside liner 48 may be composed of a substantially hydrophobic material, and the hydrophobic material may optionally be treated with a surfactant or otherwise processed to impart a desired level of wettability and hydrophilicity. The surfactant can be applied by any conventional means, such as spraying, printing, brush coating or the like. The surfactant can be applied to the entire bodyside liner 48 or can be selectively applied to particular sections of the bodyside liner, such as the medial section along the longitudinal center line.

The bodyside liner 48 may also be stretchable, and more suitably it may be elastomeric. Suitable elastomeric materials for construction of the bodyside liner 48 can include elastic strands, LYCRA elastics, cast or blown elastic films, nonwoven elastic webs, meltblown or spunbonded elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers. The bodyside liner 48 can also be made from extensible materials as are described in U.S. patent application Ser. No. 09/563,417 filed on May 3, 2000 by Roessler et al. or from biaxially stretchable materials as are described in U.S. patent application Ser. No. 09/698,512 filed on Oct. 27, 2000 by Vukos et al., both references which are hereby incorporated by reference.

As seen in FIG. 3, the illustrated absorbent structure 50 is generally rectangular. It is contemplated, however, that the absorbent structure 50 can have any suitable shape and size. For example, the absorbent structure 50 can include arcuate leg cutouts (e.g., by die cutting the absorbent structure) in the crotch region 26 of the training pant 20. While the illustrated absorbent structure 50 is shown and described herein as extending from the crotch region 26 into both the front and back waist regions 22 and 24, it is contemplated that the absorbent structure may extend from the crotch region 26 into only the front waist region 22, or only the back waist region 24, without departing from the scope of this disclosure.

The absorbent structure 50 is suitably compressible, conformable, non-irritating to a wearer's skin, and capable of absorbing and retaining liquids and certain body wastes. For example, the absorbent structure 50 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent structure comprises a matrix of cellulosic fluff and superabsorbent hydrogel-forming particles. The cellulosic fluff may include a blend of wood pulp fluff. Suitable types of fluff include, for example, fluff pulp commercially available from Weyerhaeuser Company under the designation FR416 (7.5 percent Moisture) and CF416 (7.5 percent Moisture). Weyerhaeuser Company has offices in Federal Way, Wash., U.S.A.

The materials may be formed into a web structure by employing various conventional methods and techniques. For example, the absorbent structure 50 may be formed by a dry-forming technique, an air forming technique, a wet-forming technique, a foam-forming technique, or the like, as well as combinations thereof. Methods and apparatus for carrying out such techniques are well known in the art. Furthermore, the absorbent structure 50 may itself encompass multiple layers in a Z-direction (e.g., thickness) of the absorbent structure 50. Such multiple layers may take advantage of differences in absorbent capacity, such as by placing a lower absorbent capacity material layer closer to the liner 48 and a higher absorbent capacity material closer to the backsheet 46. Likewise, discrete portions of a single-layered absorbent structure may encompass higher capacity absorbents, and other discrete portions of the structure may encompass lower capacity absorbents.

Superabsorbent material is suitably present in the absorbent structure 50 in an amount of from about 0 to about 100 weight percent based on total weight of the absorbent structure 50. The absorbent structure 50 may suitably have a density within the range of about 0.10 to about 0.60 grams per cubic centimeter. Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and preferably is capable of absorbing more than about 25 times its weight in liquid. Suitable superabsorbent materials are readily available from various suppliers. For example, Hysorb T 9700 superabsorbent, which is commercially available from BASF of Ludwigshafen, Germany, or Favor SXM 5600 superabsorbent, which is commercially available from Evonik of Essen, Germany.

The absorbent structure 50 may comprise a coform material. The term "coform material" generally refers to composite materials comprising a mixture or stabilized matrix of thermoplastic fibers and a second non-thermoplastic material. As an example, coform materials are made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference.

In one suitable embodiment, the absorbent structure 50 is stretchable so as not to inhibit the stretchability of other components to which the absorbent structure may be adhered, such as the backsheet 46 and bodyside liner 48. After being formed or cut to a desired shape, the absorbent structure 50 may be wrapped or encompassed by a suitable wrap (not shown) that aids in maintaining the integrity and shape of the absorbent structure.

The absorbent assembly 36 is configured to contain and/or absorb exudates discharged from the wearer. For example, the containment flaps 52 are configured to provide a barrier to the transverse flow of body exudates. A flap elastic member 72 (FIG. 3) may be operatively joined with each containment flap 52. The elasticized containment flaps 52 define a partially unattached, or free, edge which assumes an upright configuration in at least the crotch region 26 of the absorbent training pant 20 to form a seal against the wearer's body during use. In one suitable embodiment, the containment flaps 52 can be located along the side edges 28 of the training pant 20, and can extend longitudinally along the entire length of the absorbent assembly 36 or may only extend partially along the length of the absorbent assembly 36.

In the illustrated embodiment, the absorbent assembly 36 also includes a surge management layer 76, which can be seen in FIG. 3, located adjacent the absorbent structure 50 (e.g., between the absorbent structure 50 and the liner 48). The surge management layer 76 helps to decelerate and diffuse surges or gushes of liquid that may be rapidly introduced into the absorbent structure 50 of the training pant 20 by the wearer. Desirably, the surge management layer 76 can rapidly accept and temporarily hold the liquid prior to releasing the liquid into the storage or retention portions of the absorbent structure 50. Examples of suitable surge management layers are described in U.S. Pat. No. 5,486,166 issued Jan. 23, 1996 to Bishop et al.; U.S. Pat. No. 5,490,846 issued Feb. 13, 1996 to Ellis et al.; and U.S. Pat. No. 5,820,973 issued Oct. 13, 1998 to Dodge, II et al., the entire disclosures of which are hereby incorporated by reference herein.

The training pant 20 of the illustrated embodiment has a pair of refastening seams 70 disposed on the side of the pant (one seam being illustrated in FIG. 1). It is understood, however, that the seams can be located at any suitable location on the pant, and that the seams can be permanently attached (e.g., by adhesive, ultrasonic bonding, pressure bonding, thermal bonding). One suitable example of permanently attached side seams is described in U.S. patent application Ser. No. 14/091,829 filed Nov. 27, 2013 by Schoultz et al., the disclosure of which is hereby incorporated by reference in its entirety. Moreover, while the illustrated refastening seams 70 are defined by loop fastening components 90 (broadly, a "first fastening component") selectively engageable with hook fastening components 92 (broadly, a "second fastening component"), it is contemplated that any suitable refastenable fasteners can be used such as other types of mechanical fasteners, adhesive fasteners, cohesive fasteners.

With the training pant 20 in a fastened condition, partially illustrated in FIG. 1, the front and back waist regions 22, 24 are attached to each other by the first and second fastening components 90, 92 to define a wear configuration of the pant, having a waist opening 66 and a pair of leg openings 68. The waist edges 30, 32 of the absorbent training pant 20 are configured to encircle the waist of the wearer and together define the waist opening 66 (FIG. 1). Portions of the side edges 28 in the crotch region 26 generally define the leg openings 68.

As seen in FIG. 1, the training pant 20 includes an elasticized waistband system, indicated generally at 21, configured to fully encircle the waist of the wearer during use. Referring to FIGS. 1-3, the elasticized waistband system 21 of the illustrated embodiment includes a bodyside front waist elastic member 94, a bodyside rear waist elastic member 96, a garment-side front waist elastic member 98, and a garment-side rear waist elastic member 100. The waist elastic members 94, 96, 98, 100 can be formed of any suitable elastic material. Exemplary suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. Suitable elastic materials from which the waist elastic members 94, 96, 98, 100 can be formed, and suitable methods of incorporating waist elastic members into an absorbent article are described in U.S. patent application Ser. No. 14/068,918 filed Oct. 31, 2013 by Sina et al., and U.S. patent application Ser. No. 14/068,913 filed Oct. 31, 2013 by Bennett et al., incorporated by reference above.

The bodyside waist elastic members 94, 96 are attached to the body-facing side 23 of the training pant 20 (FIG. 3), and the garment-side waist elastic members 98, 100 are attached to the garment-facing side 25 of the training pant 20 (FIG. 2). In the illustrated embodiment, the waist elastic members 94, 96, 98, 100 are point bonded to the chassis 34, although the waist elastic members 94, 96, 98, 100 may be attached to the chassis 34 using any suitable attachment means such as, for example, adhesives, ultrasonic bonds, thermal bonds, and/or pressure bonds.

Although the elasticized waistband system 21 is illustrated and described as including bodyside front and rear waist elastic members 94, 96 and garment-side front and rear waist elastic members 98, 100, it is understood that in alternative embodiments the elasticized waistband system 21 may include any combination of the bodyside front waist elastic member 94, the bodyside rear waist elastic member 96, the garment-side front waist elastic member 98, and/or the garment-side rear waist elastic member 100.

As seen in FIGS. 2 and 3, the top edges of the front waist elastic members 94, 98 of the illustrated embodiment are generally aligned with the front waist edge 30 of the training pant 20, and the top edges of the rear waist elastic members 96, 100 of the illustrated embodiment are generally aligned with the back waist edge 32 of the training pant 20. Further, each of the side edges of the front and rear waist elastic members 94, 96, 98, 100 are generally aligned with the side edges 28 of training pant 20. Each of the front and rear waist elastic members 94, 96, 98, 100 extend from one side edge 28 of the training pant 20 to the other, laterally opposing side edge 28 of the training pant 20. The waist elastic members 94, 96, 98, 100 of the illustrated embodiment are configured to fully encircle the waist opening 66 (FIG. 1) and the wearer when the training pant 20 is donned in the wearing configuration.

In the illustrated embodiment and as seen in FIG. 3, leg elastic members 82 are disposed on the body-facing side 23 of the chassis 34. In the illustrated embodiment, the leg elastic members 82 are interposed between the chassis 34 and the absorbent assembly 36, although in other suitable embodiments, the leg elastic members 82 may be attached to a body-facing side of the absorbent assembly 36 in addition to the body-facing side 23 of the chassis 34 such that the absorbent assembly 36 is interposed between the leg elastic members 82 and the chassis 34. In yet other suitable embodiments, it is contemplated that the leg elastic members 82 can be disposed on the garment-facing side 25 of the chassis 34 in addition to or instead of the leg elastic members 82 disposed on the body-facing side 23. That is, in one suitable embodiment, the leg elastic members 82 can be disposed on both the body-facing and garment-facing sides 23, 25 of the chassis 34. In another suitable embodiment, the leg elastic members 82 can be disposed on either the body-facing side 23 or the garment-facing side 25 of the chassis 34.

As seen in FIG. 3, each of the leg elastic members 82 includes at least one elastic element (e.g., an elastic strand 83) and a carrier sheet 84 to facilitate attachment of the elastic elements to the training pant 20. It is contemplated, however, that the carrier sheet 84 can be omitted in some embodiments, and the elastic strands 83 can be attached directly to the training pant 20 (e.g., the chassis 34). Although the leg elastic members 82 are illustrated as having one elastic strand 83, the leg elastic members may include any suitable number of elastic elements.

The leg elastic members 82 can be formed from any suitable elastic material. Exemplary suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate.

In one suitable embodiment, for example, the leg elastic members 82 comprise a plurality of dry-spun coalesced multifilament spandex elastomeric threads sold under the trade name LYCRA® and available from Invista of Wichita, Kans., U.S.A. In another suitable embodiment, the leg elastic members 82 comprise a vertical filament laminate (VFL) material. A VFL is a composite material having at least one gatherable layer such as a non-woven material and at least one elastic layer. One type of vertical filament laminate is disclosed, for example, by U.S. Pat. No. 6,916,750 to Thomas et al., which is incorporated herein by reference. In another suitable embodiment, the leg elastic members 82 comprise an elastic nonwoven composite having an apertured elastic film laminated to one or more nonwoven web materials, examples of which are described in U.S. Pat. No. 7,803,244 issued Sep. 28, 2010 to Siqueira et al., and U.S. Pat. No. 8,361,913 issued Jan. 29, 2013 to Siqueira et al., both of which are incorporated herein by reference. Other suitable elastic materials include single- and dual-faced spandex laminates, stretch-bonded laminates (SBL), and continuous filament stretch-bonded laminates (CFSBL), examples of which are described in U.S. Pat. No. 5,385,775 issued Jan. 31, 1995 to Wright; U.S. Pat. No. 6,057,024 issued May 2, 2000 to Mleziva et al.; and U.S. Pat. No. 6,969,441 issued Nov. 29, 2005 to Welch et al., all of which are incorporated herein by reference.

In the illustrated embodiment, the leg elastic members 82 are attached (e.g., bonded) to the body-facing side 23 of the chassis 34 and positioned generally in the crotch region 26 of the absorbent training pant 20. As illustrated in FIG. 3, the leg elastic members 82 are aligned with the respective side edge 28 of the training pant 20. More specifically, each of the illustrated leg elastic members 82 is coterminous with the respective side edge 28. It is understood, however, that the leg elastic members 82 can have any suitable arrangement. The leg elastic members 82 are separated from one another by a minimum lateral distance 102 (shown in FIG. 4) along the crotch region 26 of the training pant 20. In the illustrated embodiment, the minimum lateral distance 102 is less than the width 102 of the absorbent assembly 36 such that the absorbent assembly 36 overlaps a portion of the leg elastic members 82.

In the illustrated embodiment, the absorbent assembly 36 is formed separately from the chassis 34, and attached to the chassis 34 using suitable attachment means such as, for example, adhesives, ultrasonic bonds, thermal bonds, and/or pressure bonds. Suitable adhesives can be applied continuously or intermittently as beads, a spray, parallel swirls, or the like. Suitable ultrasonic bonds, pressure bonds, and/or thermal bonds can be formed continuously or intermittently along the absorbent assembly 36 to effect the attachment of the absorbent assembly 36 to the chassis 34. In the illustrated embodiment, the absorbent assembly 36 is permanently attached to the chassis 34. The term "permanently attached" is synonymous with terms such as "permanently joined," "permanently adhered," and "permanently bonded," and is intended herein to refer to an attachment that is generally not releasable without some damage or substantially reduced functionality of the components that are permanently attached.

Because the absorbent assembly 36 is formed separately from the chassis 34, it is desirable to attach the absorbent assembly 36 to the chassis 34 along substantially the entire interface between the chassis 34 and the absorbent assembly 36 to prevent the absorbent assembly 36 from shifting or lifting away from the chassis 34 and becoming twisted or folded when donning the training pant 20 and/or during wear. However, attaching the absorbent assembly 36 to the chassis 34 proximate to the leg elastic members 82 may prevent the leg elastic members 82 from gathering or retracting effectively, thereby reducing the leakage performance of the training pant 20. Further, attaching the absorbent assembly 36 to the chassis 34 proximate to the leg elastic members 82 may restrict the elastic elongation of the chassis 34 along the regions of the chassis 34 to which the leg elastic members 82 are attached.

Figure 4:
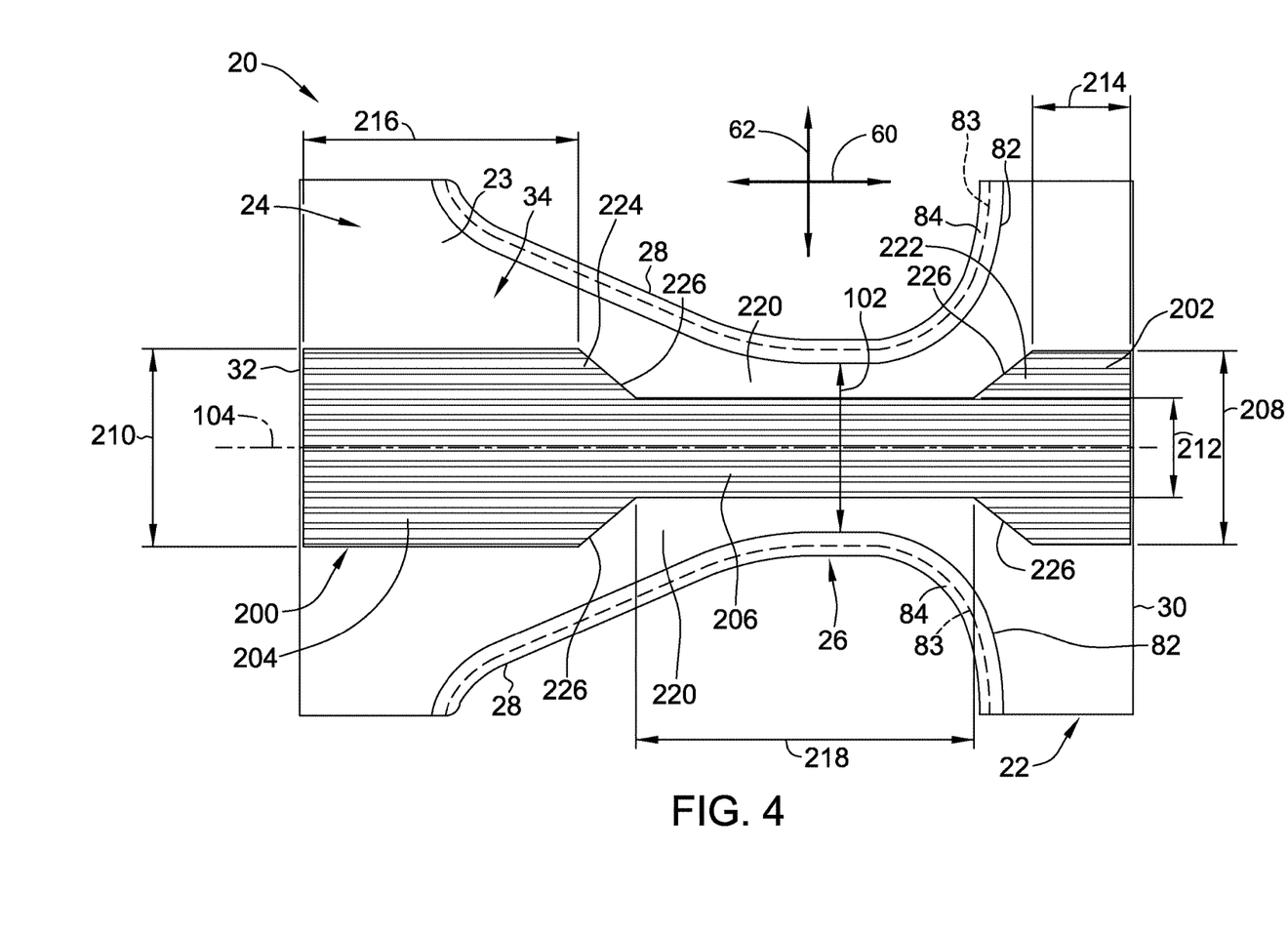
FIG. 4 is a top plan view the absorbent assembly of FIGS. 1-3 with various portions omitted to illustrate an absorbent assembly attachment area suitable for attaching the absorbent assembly to the chassis.

Referring now to FIGS. 3 and 4, the absorbent assembly 36 is attached to the chassis 34 by an absorbent assembly attachment area 200 configured to facilitate elastic retraction and elongation of the leg elastic members 82 and the chassis 34. In the illustrated embodiment, the attachment area 200 is symmetric about a longitudinal centerline 104 of the training pant 20, although it is contemplated that the attachment area may have a configuration other than symmetric about the longitudinal centerline 104 of the training pant 20.

With reference to FIG. 4, the attachment area 200 includes a front attachment zone 202, a rear attachment zone 204, and a central attachment zone 206 extending longitudinally between the front and rear attachment zones 202, 204. The front, rear, and central attachment zones 202, 204, and 206 each have a respective width 208, 210, and 212, and a respective length 214, 216, and 218.

The widths 208, 210 of the front and rear attachment zones 202, 204 are substantially equal to the width 37 of the absorbent assembly 36 such that substantially the entire surface area of the absorbent assembly 36 is attached to the chassis 34 along the front and rear attachment zones 202, 204. In other embodiments, the front and/or the rear attachment zones 202, 204 may have a width other than substantially equal to the width 37 of the absorbent assembly 36. For example, the widths 208, 210 of the front and/or the rear attachment zones 202, 204 may be less than the width 37 of the absorbent assembly 36.

In the illustrated embodiment, the widths 208, 210 of the front and rear attachment zones 202, 204 are also greater than the minimum lateral distance 102 between the leg elastic members 82. The widths 208, 210 of the front and rear attachment zones 202, 204 may be different from one another or, as illustrated in FIG. 4, the widths 208, 210 of the front and rear attachment zones 202, 204 may be substantially equal to one another.

In the illustrated embodiment, the width 212 of the central attachment zone 206 is less than both the width 208 of the front attachment zone 202 and the width of the rear attachment zone 204. In one suitable embodiment, for example, the ratio between the width 212 of the central attachment zone 206 and the width 208 of the front attachment zone 202 is less than about 0.9, more suitably less than about 0.8, and, even more suitably, less than about 0.75. In another suitable embodiment, the ratio between the width 212 of the central attachment zone 206 and the width 210 of the rear attachment zone 204 is less than about 0.9, more suitably less than about 0.8, and, even more suitably, less than about 0.75. Moreover, the width 212 of the central attachment zone 206 is less than the minimum lateral distance 102 between the leg elastic members 82, and the central attachment zone 206 extends a suitable length 218 along the training pant 20 such that the attachment area 200 does not overlap the leg elastic members 82.

Additionally, the width 212 of the central attachment zone 206 can be sized such that the central attachment zone 206 is spaced from the leg elastic members 82 to facilitate elastic expansion and retraction of the chassis 34 proximate to the leg elastic members 82. In one suitable embodiment, for example, the ratio of the width 212 of the central attachment zone 206 and the lateral distance 102 between the leg elastic members 82 taken along any lateral cross-section of the training pant 20 is less than about 0.95, more suitably less than about 0.9, and, even more suitably, less than about 0.8.

Further, in the illustrated embodiment, the width 212 of the central attachment zone 206 is less than the width 37 of the absorbent assembly 36. In one suitable embodiment, for example, the ratio of the width 212 of the central attachment zone 206 to the width 37 of the absorbent assembly 36 is between about 0.25 and about 0.80, more suitably between about 0.50 and about 0.75, and, even more suitably, between about 0.65 and about 0.75. As such, when the absorbent assembly 36 is attached to the chassis 34, the absorbent assembly 36 has laterally opposing non-attachment zones 220 (FIG. 4) that facilitate elastic retraction and elongation of the leg elastic members 82 and/or the chassis 34. More specifically, the non-attachment zones 220 comprise the portion(s) of the absorbent assembly 36 unattached to the chassis 34 along the crotch region 26 of the training pant. The non-attachment zones 220 of the absorbent assembly 36 overlap a portion of the leg elastic members 82, and thus facilitate elastic retraction and elongation of the leg elastic members 82. Further, as seen in FIG. 4, a portion of each non-attachment zone 220 extends between a respective leg elastic member 82 and the central attachment zone 206, and thus facilitates elastic retraction and elongation of the chassis 34.

In the illustrated embodiment, the attachment area 200 also includes two transition attachment zones 222, 224, one extending between the front attachment zone 202 and the central attachment zone 206, and the other extending between the rear attachment zone 204 and the central attachment zone 206. As shown in FIG. 4, the width of the transition attachment zones 222, 224 decreases as the transition attachment zones 222, 224 extend inwardly towards the central attachment zone 206. More specifically, the transition attachment zone 222 has substantially the same width as the front attachment zone 202 at an adjoining end thereof, and has substantially the same width as the central attachment zone 206 at an adjoining end thereof. Similarly, the transition attachment zone 224 has substantially the same width as the rear attachment zone 204 at an adjoining end thereof, and has substantially the same width as the central attachment zone 206 at an adjoining end thereof. The width of the attachment area 200 thereby transitions between the front and rear attachment zones 202, 204 and the central attachment zone 206 within the transition attachment zones 222, 224, and provides additional area over which the absorbent assembly 36 is attached to the chassis 34 as compared to a stepped transition between the front and rear attachment zones 202, 204 and the central attachment zone 206.

In the illustrated embodiment, the transition attachment zones 222, 224 have linear lateral outer edges 226. It is contemplated, however, that the lateral outer edges 226 of the transition attachment zones 222, 224 may have any other suitable shape, such as concave or convex. In one suitable embodiment, for example, the lateral outer edges 226 of the transition attachment zones 222, 224 are shaped complementary to the leg elastic members 82.

The transition attachment zones 222, 224 may extend any suitable length between the central attachment zone 206 and the front attachment zone 202 or the rear attachment zone 204. In one suitable embodiment, for example, the transition attachment zones 222, 224 extend to the waist edges 30, 32 of the training pant 20. In another suitable embodiment, the transition attachment zones 222, 224 extend throughout the crotch region 26 of the training pant 20 and adjoin one another.

As noted above, the absorbent assembly 36 may be attached to the chassis 34 using adhesives, ultrasonic bonds, thermal bonds, and/or pressure bonds. In embodiments in which the absorbent assembly 36 is attached to the chassis 34 using adhesives, the adhesive generally defines the attachment area 200. In one embodiment, for example, the attachment area 200 is formed by intermittently applying an adhesive (e.g., beads, parallel swirls, or spray) along the chassis 34 in the shape of the attachment area 200.

In embodiments in which the absorbent assembly 36 is attached to the chassis 34 by ultrasonic bonds, thermal bonds, and/or pressure bonds, the attachment area 200 is generally defined by the bond pattern between the chassis 34 and the absorbent assembly 36. As described above, suitable ultrasonic bonds, pressure bonds, and/or thermal bonds can be formed continuously or intermittently along the absorbent assembly 36 to effect the attachment of the absorbent assembly 36 to the chassis 34.

As described above, the attachment area 200 comprises a plurality of attachment zones 202, 204, 206, 222, and 224 which generally define the shape of the attachment area 200. As used herein, the term "attachment zone" refers to the area of the chassis 34 along which the absorbent assembly 36 is attached to the chassis 34, and the area enclosed by the outer boundaries of the attachment zone, including areas of the chassis 34 along which the absorbent assembly 36 may not be attached. Accordingly, in one suitable embodiment, at least one of the attachment zones 202, 204, 206, 222, and 224 comprises a plurality of longitudinally-extending adhesive strips spaced apart along the lateral direction 62 of the training pant 20. In another suitable embodiment, at least one of the attachment zones 202, 204, 206, 222, and 224 consists of a continuous or intermittent bond, such as an ultrasonic, thermal, or pressure bond, formed around and defining a perimeter of the attachment zone.

The absorbent assembly 36 may be attached to the chassis 34 via the backsheet 46, the bodyside liner 48, and/or the absorbent structure 50. In one suitable embodiment, for example, the bodyside liner 48 extends around the absorbent structure 50 and the backsheet 46, and both the backsheet 46 and the bodyside liner 48 are attached to the chassis 34. In another suitable embodiment, the backsheet 46 is omitted from the absorbent assembly 36, and the absorbent assembly 36 is attached to the chassis 34 via the bodyside liner 48 and/or the absorbent structure 50.

The absorbent assembly 36 can be attached to the chassis 34 over a significant portion of the surface area of the absorbent assembly 36 to facilitate maintaining the position of the absorbent assembly 36 during donning and wearing of the training pant 20. In one suitable embodiment, for example, the absorbent assembly 36 is attached to the chassis 34 over about 70% to about 99% of the surface area of the absorbent assembly 36, more suitably over about 75% to about 95% of the surface area of the absorbent assembly 36, and, even more suitably, over about 80% to about 90% of the surface area of the absorbent assembly 36.

The area of attachment between the absorbent assembly 36 and the chassis 34 varies in the different regions of the training pant. In one suitable embodiment, for example, the absorbent assembly 36 is attached to the chassis 34 in the front waist region 22 and/or the back waist region 24 over about 70% to about 100% of the surface area of the absorbent assembly 36 within the respective front or back waist region 22, 24, more suitably over about 85% to about 100% of the surface area of the absorbent assembly 36 within the respective front or back waist region 22, 24, and, even more suitably, over about 90% to about 100% of the surface area of the absorbent assembly 36 within the respective front or back waist region 22, 24. Further, in such an embodiment, the absorbent assembly 36 may be attached to the chassis 34 in the crotch region 26 over about 25% to about 80% of the surface area of the absorbent assembly 36 within the crotch region 26, more suitably between about 50% to about 80% of the surface area of the absorbent assembly 36 within the crotch region 26, and, even more suitably, over about 65% to about 80% of the surface area of the absorbent assembly 36 within the crotch region 26.

In one suitable embodiment, the length of the area of attachment between the absorbent assembly 36 and the chassis 34 extends substantially the entire length of the absorbent assembly 36. Further, the width of the area of attachment relative to the width 37 of the absorbent assembly 36 varies in the different regions of the training pant 20. In one suitable embodiment, for example, the width of the area of attachment between the absorbent assembly 36 and the chassis 34 in the front waist region 22 and/or the back waist region 24 is about 70% to 100% of the width 37 of the absorbent assembly 36, more suitably about 85% to about 100% of the width 37 of the absorbent assembly 36, and, even more suitably, about 90% to about 100% of the width 37 of the absorbent assembly 36. Further, in such an embodiment, the width of the area of attachment between the absorbent assembly 36 and the chassis 34 in the crotch region 26 is about 25% to about 80% of the width 37 of the absorbent assembly 36, more suitably about 50% to about 80% of the width 37 of the absorbent assembly 36, and, even more suitably, about 65% to about 80% of the width 37 of the absorbent assembly 36.

The zoned attachment areas described herein enable a large portion of the surface area of the absorbent assembly to be attached to the chassis, while providing suitable elastic extension and retraction within the leg elastic members and the chassis. Such zoned attachment areas thereby facilitate maintaining the position of the absorbent assembly during donning and wearing of the training pants, while allowing the leg elastic members to effectively gather and retract, and thereby form a seal around the legs of the wearer.

Although the zoned attachment areas are shown and described with reference to the training paint 20 shown and described with reference to FIGS. 1-4, it is contemplated that the zoned attachment areas described herein may be utilized with any absorbent article to secure an absorbent assembly to one or more components of the absorbent article.

Figure 5:
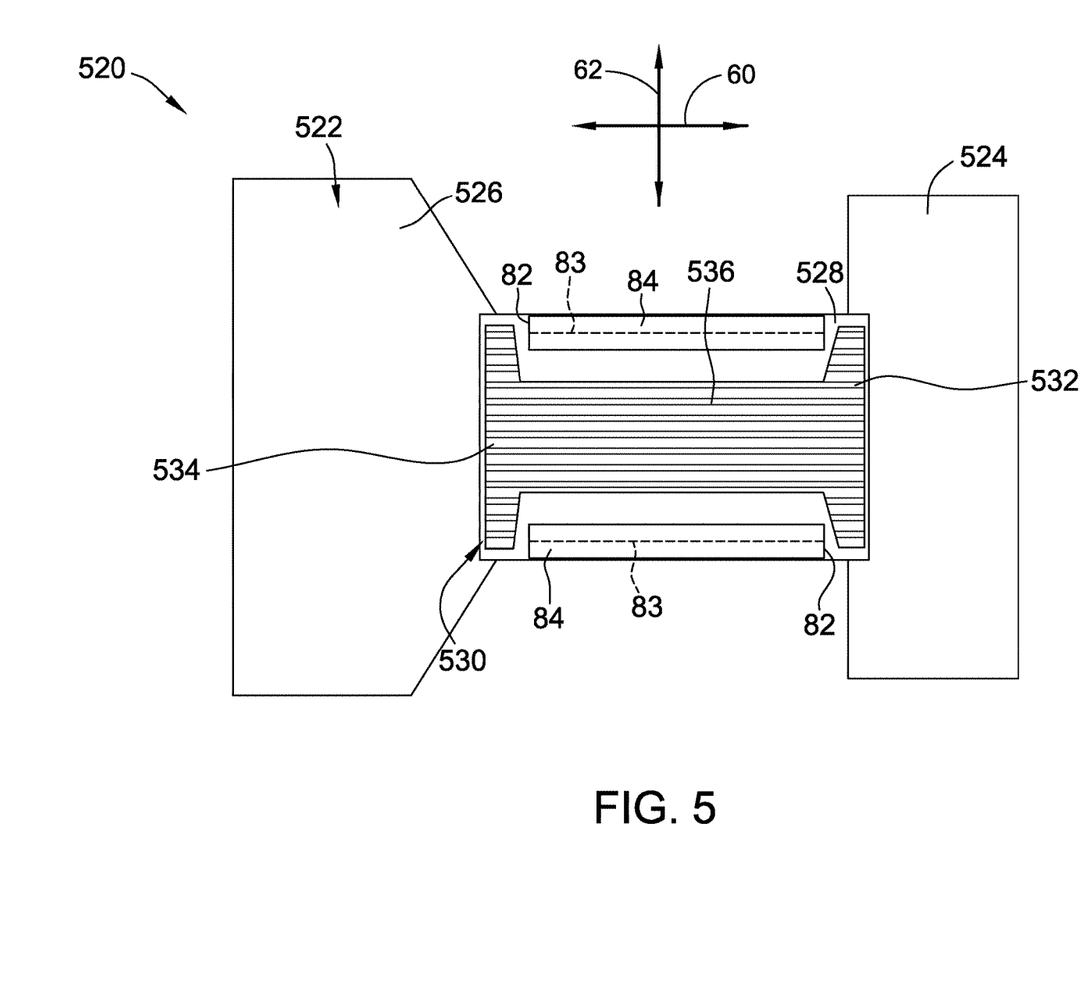
FIG. 5 is a top plan view of another suitable embodiment of an absorbent article having a multi-piece chassis and an absorbent assembly attachment area suitable for attaching an absorbent assembly to the chassis.

For example, FIG. 5 illustrates an alternative embodiment of an absorbent article, also in the form of a training pant 520, having a three-piece chassis 522. The absorbent assembly 36, the elasticized waistband system 21, and the fastening components 90, 92 are omitted from FIG. 5 for illustration.

The three-piece chassis 522 includes a front portion 524, a rear portion 526, and a central portion 528 extending between and interconnecting the front and rear portions 524 and 526. The central portion 528 is generally rectangular, although it is contemplated that the central portion can have curved or arcuately shaped sides to provide a more body confirming shape. Similarly, the front and/or rear portions 524, 526 can have curved or arcuately shaped sides to provide a more body confirming shape.

In the embodiment illustrated in FIG. 5, the front and rear portions 524, 526 are stretchable, and, more suitably, elastic in at least the transverse, or circumferential direction of the pant 520, and the central portion 528 is non-stretchable in both the transverse and the longitudinal direction. Alternatively, the central portion 528 is stretchable in the transverse direction and/or the longitudinal direction. The front, rear, and central portions 524, 526, and 528 may be constructed of either liquid permeable or liquid impermeable materials. Further, the front, rear, and central portions 524, 526, and 528 may be either vapor permeable, or vapor impermeable.

In the embodiment illustrated in FIG. 5, the absorbent assembly 36 is attached only to the non-stretchable central portion 528 of the chassis 522. As seen in FIG. 5, the absorbent assembly attachment area 530 is likewise applied only to the non-stretchable central portion 528 of the chassis 522.

Similar to the attachment area 200 shown and described with reference to FIG. 4, the attachment area 530 includes a front attachment zone 532, a rear attachment zone 534, and a central attachment zone 536 having varying widths to provide a large area of attachment between the chassis 522 and the absorbent assembly 36, while also providing suitable elastic extension and retraction within the leg elastic members 82.

Figure 6:
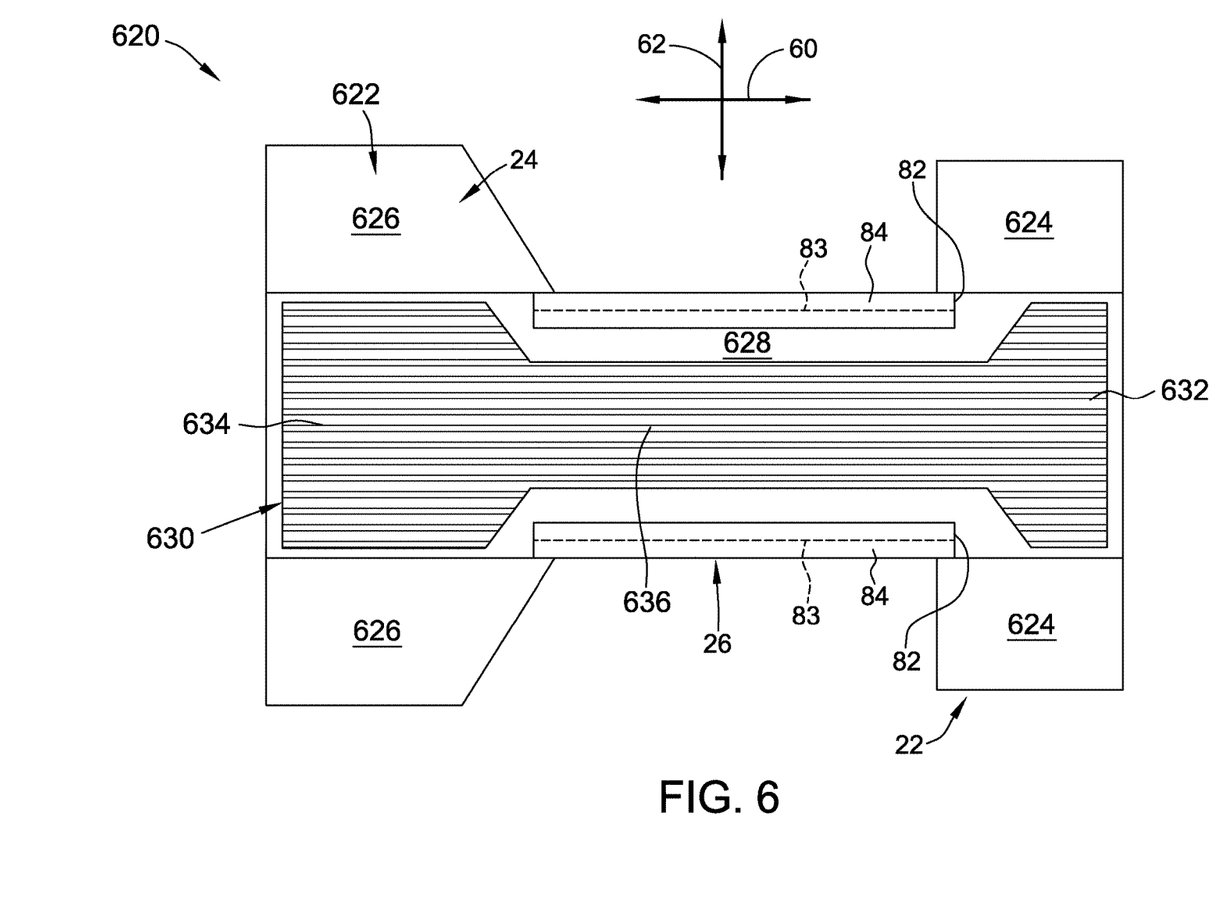
FIG. 6 is a top plan view of another suitable embodiment of an absorbent article having another embodiment of a multi-piece chassis and an absorbent assembly attachment area suitable for attaching an absorbent assembly to the chassis.

FIG. 6 illustrates another alternative embodiment of an absorbent article, also in the form of a training pant 620, having a five-piece chassis 622. The absorbent assembly 36, the elasticized waistband system 21, and fastening components 90, 92 are omitted from FIG. 6 for illustration.

The five-piece chassis 622 includes a pair of front side panels 624, a pair of rear side panels 626, and a central portion 628 extending along substantially the entire length of the training pant 620. The central portion 628 is generally rectangular, although it is contemplated that the central portion can have curved or arcuately shaped sides to provide a more body confirming shape. Similarly, the front and/or rear side panels 624, 626 can have curved or arcuately shaped sides to provide a more body confirming shape.

The front side panels 624 extend laterally outwards from opposite sides of the central portion 628 at the front waist region 22. The rear side panels 626 extend laterally outwards from opposite sides of the central portion 628 at the back waist region 24.

The front and rear side panels 624, 626 are stretchable, and, more suitably, elastic in at least the transverse, or circumferential direction of the pant 620. The central portion 628 is non-stretchable in both the transverse and the longitudinal direction. Alternatively, the central portion 628 is stretchable in the transverse direction and/or the longitudinal direction. The front and rear side panels 624, 626 and the central portion 628 may be constructed of either liquid permeable or liquid impermeable materials. Further, the front and rear side panels 624, 626 and the central portion 628 may be either vapor permeable, or vapor impermeable.

In the embodiment illustrated in FIG. 6, the absorbent assembly 36 is attached only to the non-stretchable central portion 628 of the chassis 622. As seen in FIG. 6, the absorbent assembly attachment area 630 is likewise applied only to the non-stretchable central portion 628 of the chassis 622.

Similar to the attachment area 200 shown and described with reference to FIG. 4, the attachment area 630 includes a front attachment zone 632, a rear attachment zone 634, and a central attachment zone 636 having varying widths to provide a large area of attachment between the chassis 622 and the absorbent assembly 36, while also providing suitable elastic extension and retraction within the leg elastic members 82.

To further facilitate attachment of the absorbent assembly 36, as well as elastic retraction and elongation of the leg elastic members 82 and the chassis 34, the training pant 20 can be constructed such that the peel strength and the internal cohesive strength of the attachment between the absorbent assembly 36 and the chassis 34, as determined by the test methods described below, are within desired ranges. Peel strength and internal cohesion are measures of the bond strength between component layers of laminated fabrics, as described in more detail below.

In one suitable embodiment, for example, the attachment between the absorbent assembly 36 and the chassis 34 has a peel strength of between about 75 grams-force per inch (gf/inch) and about 1000 gf/inch, more suitably between about 100 gf/inch and about 700 gf/inch, and, even more suitably, between about 225 gf/inch and about 500 gf/inch. In another suitable embodiment, the attachment between the absorbent assembly 36 and the chassis 34 has an internal cohesive strength of between about 0.5 kilograms-force per square inch ($kgf/inch^2$) and about 14.0 $kgf/inch^2$, more suitably between about 2.0 $kgf/inch^2$ and about 8.0 $kgf/inch^2$, and, even more suitably, between about 2.0 $kgf/inch^2$ and about 6.0 $kgf/inch^2$.

The following examples are provided for purposes of illustration only.

EXAMPLES

Twenty seven laminate samples were tested for peel strength and internal cohesive strength, as described below. The twenty seven laminate samples were constructed using three different types of outer cover materials and three different types of films. Each outer cover material was adhesively bonded to each film using three different amounts of adhesive, to provide a total of twenty seven different samples.

The outer cover materials included a hydroentangled spunbonded/meltblown/spunbonded ("SMS") material (hereinafter "OC Hyd. Ent. SMS"), a nonwoven film, non-stretch laminate (hereinafter "OC Nonwoven/Film Lam."), and an elastic stretch laminate (hereinafter "OC Elast. Lam."). The films included a polyethylene film having a basis weight of about 18.4 grams per square meter ("gsm") and being corona treated on a single side (referred to herein as "Film A"), a polyethylene film having a basis weight of about 18.4 gsm and being corona treated on both sides (referred to herein as "Film B"), and a polyethylene film having a basis weight of about 16 gsm and being corona treated on a single side (referred to herein as "Film C"). Three samples of each outer cover material/film combination were prepared using 2 gsm of adhesive, 5 gsm of adhesive, and 8 gsm of adhesive to provide a total of twenty seven different samples.

Test Methods

Peel Strength

The peel strength test is used to measure the attachment strength between component layers of laminated fabrics. The efficiency of bonding between component layers of a fabric is determined by measuring the force required to delaminate the fabric. As used with reference to the peel strength test, the term "delamination" refers to separation of the plies of a laminated fabric due to a failure of the bonding mechanism. The results of the peel strength test are expressed in grams force; higher numbers indicate a stronger, better bonded fabric.

Each test sample was prepared by applying a 101.6 mm (4 inch) wide piece of Masking tape, No. 2307 (commercially available from 3M Company) to the film side of the test sample near the widthwise center of the web. The tape was hand-pressed and smoothed over the surface of the test sample to ensure even attachment to the film. The test sample was then cut using a commercially available paper cutter to a width of 50.8±1.3 mm (2±0.05 inches) and a length of 152.4±1.3 mm (6±0.05 inches) long. The plies of the cut test samples were manually separated such that the outer cover material and the film were peeled apart for a distance of approximately 50 mm along the length of the test sample to provide a working area of approximately 100 mm.

The test sample was then loaded into an MTS Criterian 42 tensile tester commercially available from MTS Systems Corporation. More specifically, the test sample was clamped between a stationary grip and a moving grip in the tensile tester such that the lengthwise direction of the sample was aligned parallel to the direction of testing and force application. Further, the test sample was clamped between the grips such that there was no slack in the test sample. The free end of the outer cover material was placed in the moving grip, and the film end of the sample was placed in the stationary grip. The dimensions of the grip faces were 25.4 mm by 101.6 mm.

Once the test sample was loaded in the tensile tester, the test sample was loaded according the following parameters:

| | |
|---|---|
| Crosshead Speed | 305 ± 13 mm/minute (12 ± 0.5 inch/minute |
| Gage Length | 51 ± 1 mm (2 ± 0.05 inch) |
| Load Units | Grams-force |
| Full-Scale Load | 5 kg load cell |
| Peel Start | 16 mm |
| Peel End | 170 mm |
| Test Endpoint | 180 mm |

The average peel strength of the test sample was recorded to the nearest 0.01 gf, and the values were normalized based on the dimensions of the test samples. Operation of the tensile tester and data acquisition were carried out using MTS TestWorks® for Windows, commercially available from MTS Systems Corporation.

The peel strength tests were carried out in a controlled testing environment having a temperature of 23±2° C. (73.4±3.6° F.) and a relative humidity of 50±5%.

Internal Cohesive Strength

The internal cohesive strength test is used to measure the bond strength between layers of laminated materials or finished products. The test may be conducted either dry or wet. The efficiency of bonding is determined by measuring, to the nearest 0.01 kgf, the force required to delaminate the specimen. As used with reference to the internal cohesive strength test, the term "delamination" refers to the separation of the plies of a laminated fabric due to a failure of the bonding mechanism.

Each test sample for the internal cohesive strength test was prepared by cutting the outer cover material/film specimen to a size of approximately 50.8 mm by 101.6 mm (2 inches by 4 inches). The outer cover material side of the specimen was attached to the lower specimen platform of a commercially available cohesion tester using a piece of 50.8 mm by 114.3 mm (2 inches by 4.5 inches) double-sided adhesive tape. A pressure plate of the cohesion tester was pressed against the lower specimen platform for approximately 3 seconds at a pressure of about 60 psi to secure the specimen to the lower specimen platform. A piece of 24.5 mm by 31 mm (1 inch by 1.25 inches) piece of double-sided adhesive tape was applied to a 25.4 mm by 25.4 mm (1 inch by 1 inch) contact block of the cohesion tester. The contact block was then positioned above the lower specimen platform, and the lower specimen platform was raised and pressed against the contact block for approximately 10 seconds at a pressure of about 60 psi to secure the specimen to the piece of adhesive tape on the contact block. The lower specimen platform was then slowly lowered, and the peak load required to delaminate the layers of the specimen was recorded to the nearest 0.01 kgf using a Chatillon® digital force gauge commercially available from AMETEK Test & Calibration Instruments, and the values were normalized based on the dimensions of the test samples.

The internal cohesive strength tests were carried out in a controlled testing environment having a temperature of 23±2° C. (73.4±3.6° F.) and a relative humidity of 50±5%.

Test Results

The normalized test results of the peel strength tests and the internal cohesive strength tests for each sample are provided below in Table I and Table II, respectively.

TABLE I

Results of Peel Strength Testing (gf/inch)

| | 2 gsm | 5 gsm | 8 gsm |
|---|---|---|---|
| OC Nonwoven/Film Lam. - Film B | 145.7 | 127.0 | 133.8 |
| OC Nonwoven/Film Lam. - Film A | 128.2 | 139.3 | 143.5 |
| OC Nonwoven/Film Lam. - Film C | 166.6 | 152.4 | 145.8 |
| OC Elast. Lam. - Film B | 167.3 | 527.2 | 543.6 |
| OC Elast. Lam. - Film A | 368.8 | 495.0 | 605.2 |
| OC Elast. Lam. - Film C | 253.8 | 526.1 | 378.7 |
| OC Hyd. Ent. SMS - Film B | 97.2 | 578.6 | 798.1 |
| OC Hyd. Ent. SMS - Film A | 82.2 | 609.5 | 622.8 |
| OC Hyd. Ent. SMS - Film C | 154.3 | 666.8 | 824.2 |

TABLE II

| Results of Internal Cohesive Strength Testing (kgf/inch²) | | | |
|---|---|---|---|
| | 2 gsm | 5 gsm | 8 gsm |
| OC Elast. Lam. - Film B | 2.4 | 3.8 | 4.0 |
| OC Elast. Lam. - Film A | 3.2 | 3.4 | 3.9 |
| OC Elast. Lam. - Film C | 2.8 | 3.0 | 4.0 |
| OC Nonwoven/Film Lam. - Film B | 5.3 | 4.9 | 5.3 |
| OC Nonwoven/Film Lam. - Film A | 5.5 | 5.6 | 5.4 |
| OC Nonwoven/Film Lam. - Film C | 6.8 | 6.0 | 6.0 |
| OC Hyd. Ent. SMS - Film B | 3.7 | 9.6 | 11.7 |
| OC Hyd. Ent. SMS - Film A | 5.2 | 10.1 | 13.0 |
| OC Hyd. Ent. SMS - Film C | 5.2 | 11.7 | 10.9 |

With reference to Table I, the tested samples ranged from a minimum peel strength of 82.2 gf/inch, corresponding to the OC Hyd. Ent. SMS-Film A sample using 2 gsm of adhesive, to a maximum peel strength of 824.2 gf/inch, corresponding to the OC Hyd. Ent. SMS.-Film C sample using 8 gsm of adhesive. With reference to Table II, the tested samples ranged from a minimum internal cohesive strength of 2.4 kgf/inch², corresponding to the OC Elast. Lam.-Film B sample using 2 gsm of adhesive, to a maximum internal cohesive strength of 13.0 kgf/inch², corresponding to the OC Hyd. Ent. SMS-Film A sample using 8 gsm of adhesive.

To this end, in one embodiment the attachment between the absorbent assembly 36 and the chassis 34 has a peel strength according to the Peel Strength Test of between about 75 gf/inch and about 1000 gf/inch, more suitably between about 100 gf/inch and about 700 gf/inch, and, even more suitably, between about 225 gf/inch and about 500 gf/inch. In another embodiment, the attachment between the absorbent assembly 36 and the chassis 34 has an internal cohesive strength according to the Internal Cohesive Strength Test of between about 2.0 kgf/inch² and about 14.0 kgf/inch², more suitably between about 2.0 kgf/inch² and about 8.0 kgf/inch², and, even more suitably, between about 2.0 kgf/inch² and about 6.0 kgf/inch². As indicated in Tables I and II, samples prepared using 2 gsm of adhesive have peel strengths and internal cohesive strengths within the above-identified suitable ranges. Such ranges are generally adequate for using the training pant 20 for its intended purpose. Samples prepared using 2 gsm of adhesive can be manufactured at a lower cost compared to samples using 5 gsm and 8 gsm due to the cost of adhesive. Accordingly, in one suitable embodiment, the training pant 20 is manufactured using about 2 gsm of adhesive. More specifically, the absorbent assembly 36 is adhered to chassis 34 using about 2 gsm of adhesive.

In other suitable embodiments, the attachment between the absorbent assembly 36 and the chassis 34 can have an internal cohesive strength according to the Internal Cohesive Strength Test of less than about 2.0 kgf/inch², including, for example, an internal cohesive strength of about 0.5 kgf/inch². Internal cohesive strengths less than 2.0 kgf/inch² are particularly suitable for materials having a relatively low basis weight, and can be obtained, for example, by using less than 2 gsm of adhesive to secure the absorbent assembly 36 to the chassis 34.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An absorbent article having a longitudinal centerline, the article comprising:
    a chassis comprising a pair of side edges, the side edges being disposed on opposite sides of the chassis and converging laterally inward towards each other to define respective leg openings;
    a pair of leg elastic members, one of the leg elastic members of the pair of leg elastic members extending along one of the side edges and the other leg elastic member of the pair of leg elastic members extending along the other side edge, each of the leg elastic members being spaced from and free from intersecting the longitudinal centerline; and
    an absorbent assembly formed separately from the chassis, the absorbent assembly attached to the chassis by an attachment area comprising a front attachment zone, a rear attachment zone, and a central attachment zone extending between the front and rear attachment zones such that the attachment area extends contiguously between the central attachment zone and at least one of the front attachment zone and the rear attachment zone, the front and rear attachment zones having a first width and a second width, respectively, and the central attachment zone having a third width less than the first and second widths, the central attachment zone being spaced inboard from each of the leg elastic members.

2. The absorbent article as set forth in claim 1, wherein the ratio between the third width and at least one of the first width and the second width is less than 0.9.

3. The absorbent article as set forth in claim 1, wherein the ratio between the third width and at least one of the first width and the second width is less than 0.75.

4. The absorbent article as set forth in claim 1, wherein the absorbent assembly comprises:
    a liquid permeable bodyside liner;
    a liquid impermeable backsheet; and
    an absorbent structure disposed between the liner and the backsheet, wherein the absorbent assembly is attached to the chassis by at least one of the backsheet and the bodyside liner.

5. The absorbent article as set forth in claim 1, wherein the absorbent assembly has a surface area, the absorbent assembly attached to the chassis over about 75% to about 95% of the absorbent assembly surface area.

6. The absorbent article as set forth in claim 1, wherein the absorbent article includes a front waist region, a back waist region, and a crotch region extending between the front waist region and the back waist region, and the absorbent assembly has a surface area, the absorbent assembly attached to the chassis in the crotch region over about 25% to about 80% of the surface area of the absorbent assembly within the crotch region.

7. The absorbent article as set forth in claim 6, wherein the absorbent assembly is attached to the chassis in at least one of the front waist region and the back waist region over about 70% to 100% of the surface area of the absorbent assembly within the respective front or back waist region.

8. The absorbent article as set forth in claim 1, wherein the absorbent assembly overlaps at least a portion of the leg elastic members.

9. The absorbent article as set forth in claim 1, wherein the attachment area further comprises a transition attachment zone extending between the central attachment zone and one of the front attachment zone and the rear attachment zone.

10. The absorbent article as set forth in claim 9, wherein the transition attachment zone has a width that decreases as the transition attachment zone extends towards the central attachment zone.

11. The absorbent article as set forth in claim 1, wherein the attachment between the absorbent assembly and the chassis has a peel strength of between about 75 grams-force per inch and about 1000 grams-force per inch.

12. The absorbent article as set forth in claim 1, wherein the attachment between the absorbent assembly and the chassis has an internal cohesive strength of between about 0.5 kilograms-force per square inch and about 14 kilograms-force per square inch.

13. The absorbent article as set forth in claim 1, wherein the attachment area comprises an adhesive.

14. An absorbent article having a longitudinal centerline, the article comprising:
- a chassis comprising a pair of side edges, the side edges being disposed on opposite sides of the chassis and converging laterally inward towards each other to define respective leg openings;
- a pair of leg elastic members, one of the leg elastic members of the pair of leg elastic members extending along one of the side edges and the other leg elastic member of the pair of leg elastic members extending along the other side edge, each of the leg elastic members being spaced from and free from intersecting the longitudinal centerline; and
- an absorbent assembly formed separately from the chassis, the absorbent assembly attached to the chassis by an attachment area comprising a front attachment zone, a rear attachment zone, and a central attachment zone extending between the front and rear attachment zones such that the attachment area extends contiguously between the central attachment zone and at least one of the front attachment zone and the rear attachment zone, the front and rear attachment zones having a first width and a second width, respectively, and the central attachment zone having a third width less than the first and second widths, the central attachment zone being spaced inboard from each of the leg elastic members, the first and second widths of the front and rear attachment zones being less than a minimum lateral distance between the leg elastic members.

15. The absorbent article as set forth in claim 14, wherein the absorbent assembly overlaps at least a portion of each leg elastic member.

16. The absorbent article as set forth in claim 15, wherein the zone of reduced width is disposed between the portions of the leg elastic members overlapping the absorbent assembly.

17. The absorbent article as set forth in claim 14, wherein the leg elastic members are separated by a first width and the zone of reduced width has a second width, wherein the ratio between the second width and the first width is less than 0.95.

18. The absorbent article as set forth in claim 14, wherein each leg elastic member comprises a carrier sheet and an elastic element attached to the carrier sheet.

19. The absorbent article as set forth in claim 14, wherein the attachment area further comprises a front attachment zone and a rear attachment zone, the zone of reduced width disposed between the front attachment zone and the rear attachment zone.

20. The absorbent article as set forth in claim 1, wherein each of the leg elastic members are coterminous with a respective one of the side edges of the chassis.

\* \* \* \* \*